(12) United States Patent
Fisher et al.

(10) Patent No.: US 7,141,238 B2
(45) Date of Patent: *Nov. 28, 2006

(54) COMPOSITIONS FOR REDUCING UV-INDUCED INHIBITION OF COLLAGEN BIOSYNTHESIS IN HUMAN SKIN

(75) Inventors: Gary J. Fisher, Ann Arbor, MI (US); John J. Voorhees, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 198 days.

This patent is subject to a terminal disclaimer.

(21) Appl. No.: 10/691,076

(22) Filed: Oct. 22, 2003

(65) Prior Publication Data

US 2004/0208836 A1   Oct. 21, 2004

Related U.S. Application Data

(62) Division of application No. 09/285,860, filed on Apr. 2, 1999, now Pat. No. 6,683,069.

(60) Provisional application No. 60/080,437, filed on Apr. 2, 1998.

(51) Int. Cl.
*A61K 7/42* (2006.01)
*A61K 7/00* (2006.01)
*A61K 31/07* (2006.01)
*A61K 31/35* (2006.01)
*A61K 31/185* (2006.01)

(52) U.S. Cl. .................. 424/59; 424/60; 424/400; 424/401; 514/167; 514/456; 514/576; 514/629; 514/725

(58) Field of Classification Search .................. 424/59, 424/60, 400, 401; 514/167, 456, 576, 629, 514/725
See application file for complete search history.

(56) References Cited

U.S. PATENT DOCUMENTS 6,683,069 B1 * 1/2004 Fisher et al. ................ 514/167

* cited by examiner

*Primary Examiner*—Shelley A. Dodson
(74) *Attorney, Agent, or Firm*—Bradley N. Ruben

(57) ABSTRACT

Exposure of human skin to ultraviolet (UV) radiation from the sun not only induces the production of enzymes (matrix metalloproteinases) that degrade collagen, but also inhibits the synthesis of new collagen by inhibiting the synthesis of procollagen. This UV-induced inhibition of the synthesis of collagen can be prevented by the topical application of a retinoid or c-JUN inhibitor to the skin prior to exposure to UV radiation.

16 Claims, 19 Drawing Sheets

ACUTE UV (2MED) REDUCES TYPE I PROCOLLAGEN mRNA EXPRESSION IN HUMAN SKIN *IN VIVO: IN SITU* HYBRIDIZATION a NO UV    b 8HRS POST UV    c 24HRS POST UV d 48HRS POST UV    e 72HRS POST UV

UV (2MED) RAPIDLY INHIBITS TYPE I PROCOLLAGEN SYNTHESIS IN HUMAN SKIN *IN VIVO*: IMMUNOHISTOLOGY

HOURS POST (2MED)

UV (2MED) ALTERS TYPE III PROCOLLAGEN SYNTHESIS IN HUMAN SKIN *IN VIVO: IN SITU* HYBRIDIZATION a NO UV  b 8 HRS POST UV  c 24 HRS POST UV d 48 HRS POST UV  e 72 HRS POST UV

UV (2MED) RAPIDLY INHIBITS TYPE III PROCOLLAGEN SYNTHESIS IN HUMAN SKIN *IN VIVO*: IMMUNOHISTOLOGY

HOURS POST (2MED)

COMPOSITIONS FOR REDUCING UV-INDUCED INHIBITION OF COLLAGEN BIOSYNTHESIS IN HUMAN SKIN

RELATED APPLICATIONS

This application is a divisional of application Ser. No. 09/285,860, filed 2 Apr. 1999, now U.S. Pat. No. 6,683,069, which is based on provisional application 60/080,437, filed 2 Apr. 1998, the disclosures of which are both incorporated herein by reference.

BACKGROUND OF THE INVENTION

1. The Field of the Invention

This invention is in the field of photoprotection of human skin. More particularly, the invention relates to compositions and methods for this use by topical application to reduce if not eliminate the inhibition of collagen synthesis in human skin after incidental and/or direct exposure to UV radiation as would occur daily, and as would occur after recreational exposure to UV radiation during a planned, extended period in the sun.

2. The State of the Art.

Human skin is a complex organ which extends over the entire body. There are different types of skin at different portions of the body; for example, facial skin is different from that of the scalp, and even the skin on the front (palm) of the hand is different than that on the back of the hand. Although the type of skin can vary over a person's body, skin is generally composed of two main layers of tissue. The epidermis, the outermost layer, is composed of several layers. The dermis, corium, or cutis vera, the true skin, is composed of a papillary layer above and a reticular layer below.

As far as mammals go, humans are essentially hairless; that is, most of the skin of the human body can be seen without interference from hair. The skin is thus exposed to whatever insults (natural and man-made) the environment harbors. Since it was first understood that the sun caused erythema, people have taken measures to avoid its "harmful rays." There is a difference between the physiology of chronologically-aged or intrinsically-aged skin (old skin) in comparison with that of photoaged skin. Old skin typically maintains a smooth and unblemished appearance, in comparison with the leathery, blotchy, and often fine and deep wrinkling of photoaged skin. The epidermis of old skin is typically thinner than normal, whereas that of photoaged aged skin can often be thicker than normal (acanthotic) and then atrophies over time. See also N. A. Fenske and C. W. Lober, "Structural and functional changes of normal aging skin," *J. Am. Acad. Dermatol.*, 15:571–585 (1986).

Photoaging is a term presently used to describe the changes in appearance and/or function of human skin as a result of repeated exposure to sunlight, and especially in reference to wrinkles and other changes in the appearance of the skin thought to be related to exposure to the sun. The ultraviolet (UV) component of sunlight, particularly UVA and UVB, is generally believed to be the principal causative agent in photoaging. The extent of UV exposure required to cause "photoaging" is not currently known, although the amount sufficient to cause erythema (reddening, commonly seen as sunburn) in human skin is quantified empirically as the "minimal erythemal dose" ("MED") from a given UV source. Repeated exposure to sunlight UV at levels that cause erythema and tanning are, nevertheless, commonly associated with photoaging.

Solar radiation reaching the earth's surface that effects and enables various animals, including humans, comprises ultraviolet (UV) ($\lambda$<400 nm), visible (400 nm<$\lambda$<700 nm), and infrared (IR) ($\lambda$>700 nm). UV radiation is generally divided into UVA (320–400 nm), UVB (290–320 nm), and UVC (<290 nm); UVC radiation is blocked from reaching the earth's surface by stratospheric ozone. UVB doses in the range of 30–50 mJ/cm$^2$ skin cause erythema in most fair-skinned people. Sunlight reaching the surface of the earth when the sun is essentially overhead provides the following amounts of radiation: 0.5% UVB; 6.5% UVA; 38.9% visible light; and 54.0% IR. These radiation types provide the following energy fluxes: 2.11 mJ/cm$^2$·s (21.1 W/m$^2$) for UVB; 8.57 mJ/cm$^2$·s (85.7 W/m$^2$) for UVA; 53.2 mJ/cm$^2$·s (532 W/m$^2$) for visible light; and 72.2 mJ/cm$^2$·s (722 W/m$^2$) for IR.

Photoaging is characterized clinically by coarseness, wrinkles, mottled pigmentation, sallowness, laxity, telangiectasia, lentigines, purpura and relative ease of bruising, atrophy, depigmented areas, eventually premalignant, and ultimately malignant neoplasms. Photoaging commonly occurs in skin that is habitually exposed to sunlight such as the face, ears, bald areas of the scalp, neck, forearms, and hands.

Sunscreens are commonly used to prevent sunburn (erythema) of skin areas that are exposed to sunlight. Sunscreens are topical preparations that contain ingredients that absorb, reflect, and/or scatter UV light. Some sunscreens are based on opaque particulate materials, among them zinc oxide, titanium oxide, clays, and ferric chloride. Because such preparations are visible and occlusive, many people consider these opaque formulations cosmetically unacceptable. Other sunscreens contain chemicals such as p-aminobenzoic acid (PABA), oxybenzone, dioxybenzone, ethylhexyl-methoxy cinnamate, octocrylene, octyl methoxycinnamate, and butylmethoxydibenzoylmethane that are transparent or translucent on the skin. While these types of sunscreens may be more acceptable cosmetically, they are still relatively short-lived and susceptible to being removed by washing or perspiration.

As noted above, the generally accepted etiology of photodamage to skin involves an exposure to sunlight sufficient to cause erythema (sunburn or reddening; literally a flush upon the skin), and it is now known that sufficient UV radiation causes erythema. This philosophy dictates that present compositions and methods for inhibiting photoaging include the use of compounds that block or absorb UV, and that such compositions need be used only when there is a sufficient likelihood that exposure to sunlight will result in erythema. More recent sunscreen compositions include combinations of compounds that block both UVA and UVB radiation.

According to *Physiology, Biochemistry, and Molecular Biology of the Skin,* 2nd Ed., ed. by L. A. Goldsmith (New York: Oxford Univ. Press, 1991), UVA is considered both melanogenic and erythemogenic and UVA exposure induces synthesis of a 32 kDa stress protein in cultured fibroblasts. This text further describes that after a latent period of several hours after UV irradiation erythema becomes apparent (i.e., "delayed" erythema); "immediate" erythema is described as usually not apparent after UVB or UVC exposures but does occur, in a dose-dependent manner, after exposure to UVA. Goldsmith teaches that 250–290 nm (UVC region) is considered to be the most erythemogenic radiation with one thousand-fold less erythema at 290–340 nm (UVB and UVA1 region); erythema from UVB/C is taught to be a function of the total radiation exposure rather the intensity of the radiation exposure.

Retinoids have been used to retard the effects of photoaging in skin appearing to have been damaged by exposure to the sun. U.S. Pat. No. 4,877,805 describes the treatment of photoaged skin after photoaging has become apparent clinically. This patent indicates there is little point in beginning the application of a retinoid to treat photodamaged skin until the effects of photoaging begin to appear.

On the other hand, our patent applications (based on copending U.S. patent application Ser. No. 08/588,771, filed Jan. 19, 1996, and provisional application 60/048,520, filed Jun. 4, 1997, and 60/057,976, filed Sep. 5, 1997, all related to photoaging of human skin, the disclosures of which are incorporated herein by reference for all purposes) describe the damage matrix metalloproteinases (MMPs) do to skin, that their activity is greatly enhanced after exposure to UV radiation, and that photoaging can and should be treated prior to the unambiguous clinical appearance of photoaging. These patent applications describe treatment of photoaged skin (i.e., skin that has been exposed to solar UV radiation, regardless of whether erythema or the clinical signs of photoaging are apparent) by the topical administration of inhibitors of MMPs (i.e., direct inhibitors of the proteinase) and of transcription factors (e.g., inhibitors of AP-1) that affect MMP expression.

In view of the foregoing, it can be argued that the art adheres presently to the philosophy that sunlight, especially UV radiation, causes erythema, and that repeated episodes of erythema and similarly chronic exposure to the sun result in photoaged skin. This philosophy is based on the observation that people who have spent significant amounts of time in the sun have skin that appears aged, as if these people where chronologically older. As noted above, though, certain physiological differences between old skin and photoaged skin are apparent when histology and similarly direct measurements of the skin are taken.

It can be seen that the art has concentrated on preventing and repairing perceived damage to skin that appears aged because of chronic UV exposure. Sunscreens can prevent erythema, and this is generally considered sufficient for protection from the sun. The aforementioned patents teach treating photodamaged skin (although our patent defines photodamage by the presence of elevated MMPs, whereas Kligman's patent defines photodamage by clinical appearance).

Heretofore, nothing in the art has appeared to address what effect, if any, exposure to sunlight, and particularly the UV portion of the sun's spectrum, has on the production of collagen. Collagen is a polypeptide represented by the repeating peptides $[-X-Y-Gly-]_n$ where Gly is glycine and X and Y are other amino acids. About 20% of the remaining amino acids are an equal amount of proline and 4-hydroxyproline; analysis for hydroxyproline, because it is an unusual amino acid, is one method for assaying collagen or procollagen amounts. Collagen also contains other unusual amino acids, such as 3-hydroxyproline and hydroxylysine. Nineteen different types of collagen have been identified. Collagen Types I (85+%) and III (8+%) are the predominant types of collagen in human skin and are present as fibrils. Structurally, three collagen polypeptides wrap around each other in a helix to form a triple helix collagen molecule. These molecules are packed in a five-stranded rope-like structure wherein each collagen molecule is quarter-staggered with respect to the next to form a microfibril. Microfibrils are subsequently wrapped around other microfibrils to form fibrils, which in turn wrap around other fibrils to produce even larger fibers. The production of collagen fibers in vivo requires activation of the collagen biosynthesis pathway by which transcription in the cell nucleus promotes polypeptide synthesis via translation from mRNA, organization of the polypeptides into a procollagen triple helix in the cytoplasm, secretion of procollagen from the cell, and then cleavage reactions, fibril assembly, and cross-linking extracellularly. Unlike many proteins that are stored in secretory granules and then secreted from the cell upon demand, collagen is secreted continuously. According to Goldsmith, *op. cit.* (at 492), not only do retinoic acid, glucocorticoids, and vitamin $D_3$ derivatives all decrease collagen synthesis, but so do other retinoids.

SUMMARY OF THE INVENTION

Unappreciated by the art, we have found that exposure to UV radiation, whether or not sufficient to cause erythema, results in a rather complete and temporary loss of collagen synthesis. This loss of collagen synthesis is based on our findings that both the mRNA for Types I and III procollagen and the Types I and III procollagen proteins are reduced if not eliminated from fibroblasts and elsewhere in the skin after exposure to UV radiation, whether or not the UV radiation is sufficient to cause erythema in a single exposure.

In light of these findings, our invention generally can be summarized as the topical administration of a retinoid in an amount effective to reduce the inhibition of collagen synthesis mediated by exposure to UV radiation by applying the retinoid to the skin at least about 16 hours prior to exposure.

In one embodiment, our invention ameliorates the inhibition of collagen synthesis caused by recreational exposure (i.e., prolonged exposure) to UV radiation of at least one MED (minimal erythemal dose), such as would typically occur when one spends a significant portion of the daylight hours in sunlight.

In another embodiment, our invention ameliorates the inhibition of collagen synthesis caused by incidental exposure to UV radiation generally less than one MED, as would typically occur on a daily basis with such normal activities as commuting to and from work or school.

DESCRIPTION OF PREFERRED EMBODIMENTS

Figure 1:
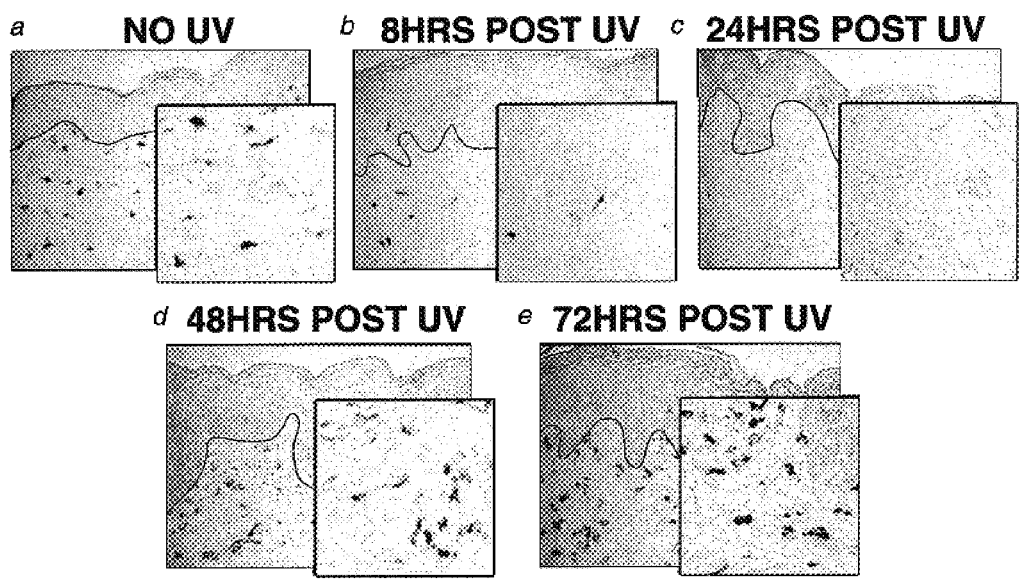
FIGS. 1A–1E depict cross-sections of biopsies of human skin stained for the expression of Type I procollagen mRNA as a function of time after exposure to UV radiation.

Collagen is, for all intents and purposes, the structural compound that supports the skin. Collagen precursor molecules are synthesized in fibroblasts in the dermis; fibroblasts are the only cells in the dermis to produce collagen.

Fibroblasts are trophic to the epidermis; under normal conditions they secrete a number of growth factors (e.g., FGF, IGF, and KGF, among others) and produce procollagen that enters the dermal matrix to become structural collagen. Procollagen is a soluble collagen precursor secreted from fibroblasts and then converted extracellularly into insoluble collagen, the primary extracellular structural component of human skin. After being secreted, the procollagen protein's carboxy terminus is cleaved to produce the pN collagen precursor protein; thereafter, the amino terminus of the precursor protein is cleaved to produce insoluble collagen, which is incorporated into the extracellular dermal matrix. While there are a number of different types of collagen and procollagens from which they are derived, Types I and III constitute the vast majority (93+%) of the total collagen in the skin. Type I procollagen migrates to the dermis-epidermis junction, where it is converted into Type I collagen. Type III procollagen is converted in the dermis into Type III collagen, which is then found throughout the dermis.

We first discovered that exposure to 2 MEDs of UV radiation eventually eliminated procollagen synthesis in human skin. One MED, or minimal erythemal dose, is the minimum dose of radiation required to cause reddening of human skin. For a constant source of illumination, such as a UV bulb, the quantity of UV radiation with which a person is illuminated is a function of the duration of exposure. In real life exposure to the sun, one MED will be a function of the time of day, cloud cover, humidity, air quality, and other factors. One MED is generally equivalent to an exposure of skin to the sun on a clear day for about 15 minutes when the sun is essentially overhead.

Our investigations relied on a number of human volunteers (all having given prior informed consent), generally ages 20 to 50, whose skin was exposed to UV radiation and then biopsied for further analysis. Except where otherwise indicated, in the following experiments four F36T12 ERE-VHO UV bulbs were used to irradiate human skin. At all times, a Kodocel TA401/407 filter was mounted 4 cm in front of the bulbs to remove UVC radiation (<290 nm). Radiation intensity was monitored using an IL443 phototherapy radiometer and an SED240/UVB/W photodetector (International Light, Newbury, Mass.). Spectroradiometry was performed using an Optronic Laboratories OL 754 system. Total irradiance (290–800 nm) at about 43 cm (17 in.) from the source of four bulbs was about 1.5 mJ/cm$^2$·s ($1.49 \times 10^{-3}$ W/cm$^2$). The radiation output from the bulbs was determined by spectroradiometry to provide about 47% UVB and about 27% UVA (composed of about 9% UVA$_1$ (340–400 nm) and about 18% UVA$_2$ (320–340 nm)), the remainder being visible and IR radiation. An exposure of about 160 seconds under this set of four bulbs is equivalent to an exposure of one MED. Accordingly, when compared with the total radiation from natural sunlight that reaches earth's surface, which radiation has about 0.5% UVB and 6.5% UVA, it can be seen that the set of four bulbs used in these experiments provides far less UVA radiation than would exposure to the sun of an equivalent amount of UVB.

Effect of UV Radiation on Collagen Synthesis

We exposed volunteers to 2 MED of UV radiation on specific areas of their hips or buttocks (i.e., areas typically not exposed to the sun on a chronic basis or incidental basis) and biopsied the area on each volunteer both prior to exposure and thereafter at 8, 24, 48, and 72 hours after exposure. As shown in FIG. 1, when these biopsies were analyzed by the riboprobe in situ hybridization technique to reveal the mRNA that encodes Types I and III procollagens, the results were striking. As shown by the staining in FIG. 1A, prior to UV exposure, fibroblasts in the dermis have Type I procollagen mRNA in their nuclei. Eight hours after exposure to 2 MED there is a significant reduction in the amount of procollagen I mRNA in the fibroblasts' nuclei (FIG. 1B), and 24 hours after exposure there is no discernable amount of mRNA revealed in the cells (FIG. 1C). Accordingly, the pathways that promote normal collagen synthesis are effectively stopped 24 hours after exposure to 2 MEDs of exposure to UV radiation. As described in the aforementioned photoaging patent applications, exposure to UV radiation also induces the production of MMPs (matrix metalloproteinases), enzymes that degrade collagen. Thus, UV radiation undermines the structure of the skin by both stimulating degradation of collagen and inhibiting collagen synthesis. The amount of procollagen I mRNA appears greater forty-eight hours after UV exposure (FIG. 1D) than before UV exposure (FIG. 1A), and there is an even more pronounced increase in the amount of the procollagen I mRNA 72 hours after exposure (FIG. 1E), as if the skin were healing a wound.

Figure 2:
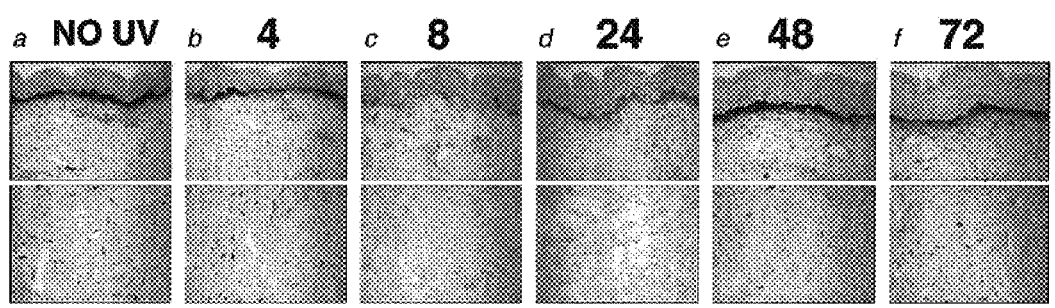
FIGS. 2A–2F depict cross-sections of biopsies of human skin stained for the presence of Type I procollagen protein as a function of time after exposure to UV radiation.

FIGS. 2A–2F are analogous to FIGS. 1A–E and depict immunohistological staining of the Type I procollagen protein in the skin. Consistent with FIG. 1, without UV exposure the procollagen I protein is present in the fibroblasts and at the papillary dermis (dermis-epidermis junction), as seen by the dark band in FIG. 2A. Four hours after UV exposure, the amount of Type I procollagen protein is reduced in both areas (FIG. 2B), and between 8 and 24 hours after exposure there is no discernable presence of Type I procollagen in the skin (FIGS. 2C and 2D, respectively). Similarly, the amount of Type I procollagen present in the skin is greater 48 and 72 hours after exposure (FIGS. 2E and 2F) than prior to exposure; this appears to be a "rebound" effect.

Figure 3:
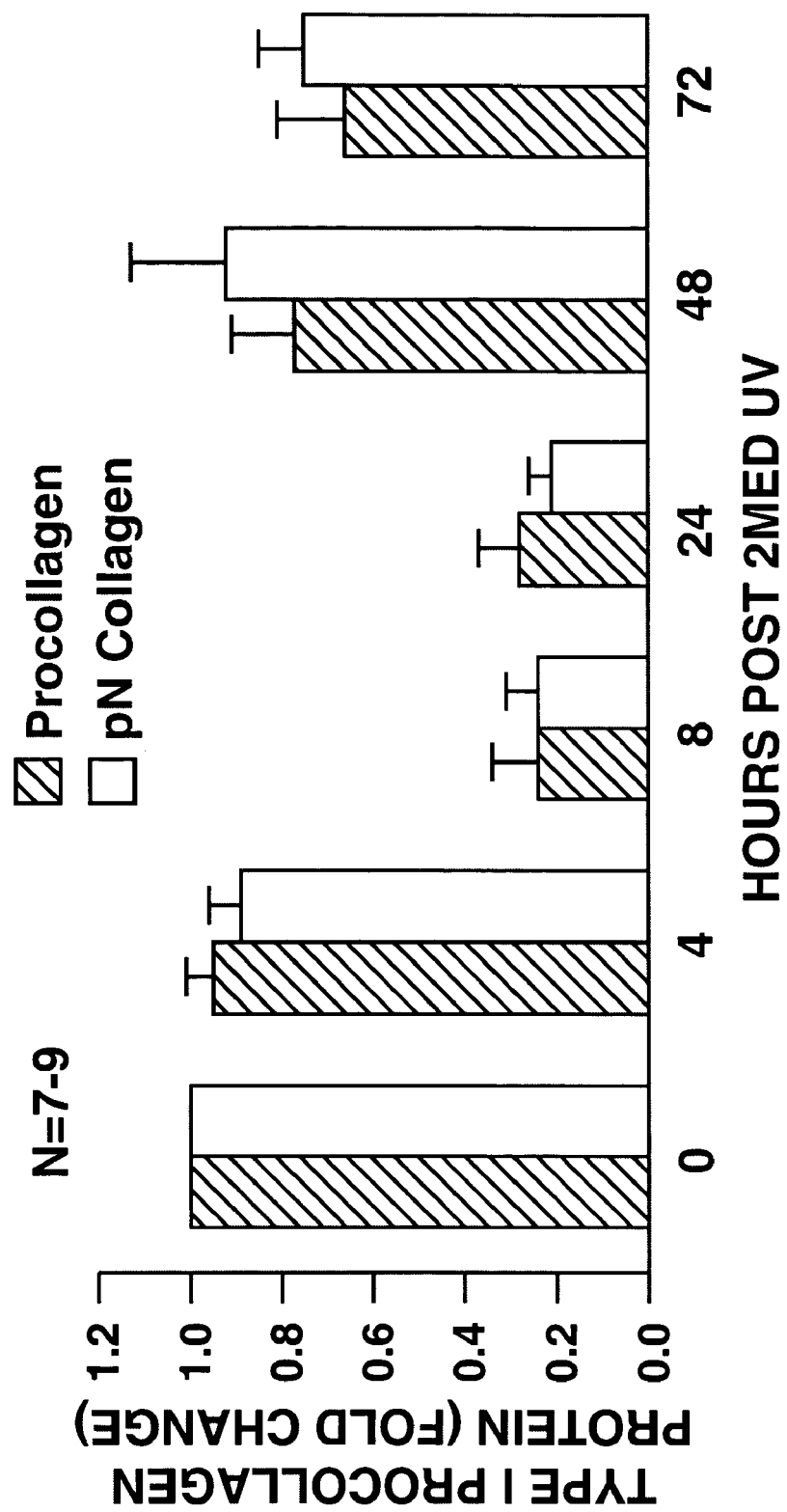
FIG. 3 is a histogram showing the results of Western analysis for Type I procollagen protein in human skin in vivo as a function of time after exposure to UV radiation.
Figure 4:
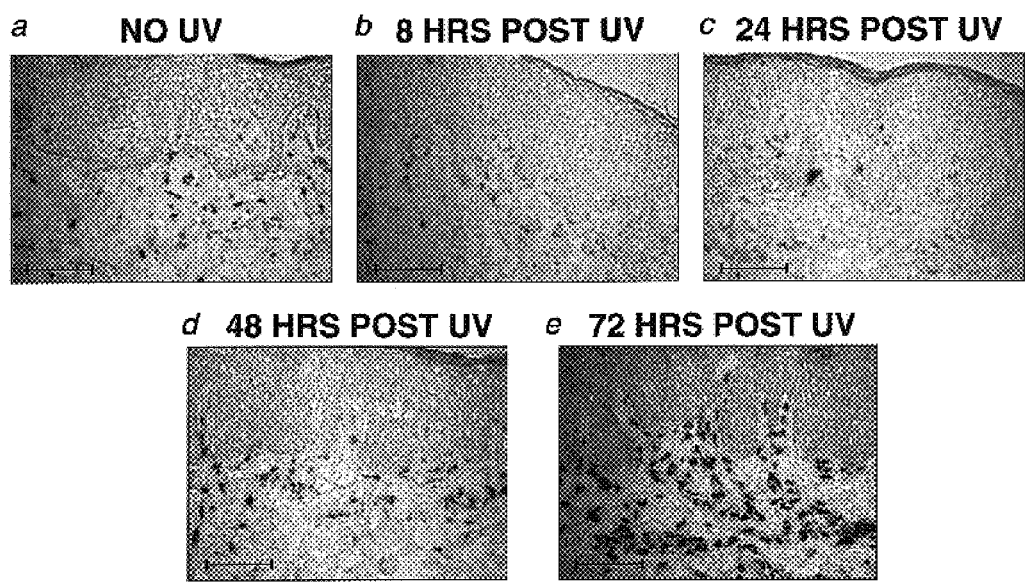
FIGS. 4A–4E depict cross-sections of biopsies of human skin stained for the expression of Type III procollagen mRNA as a function of time after exposure to UV radiation.
Figure 5:
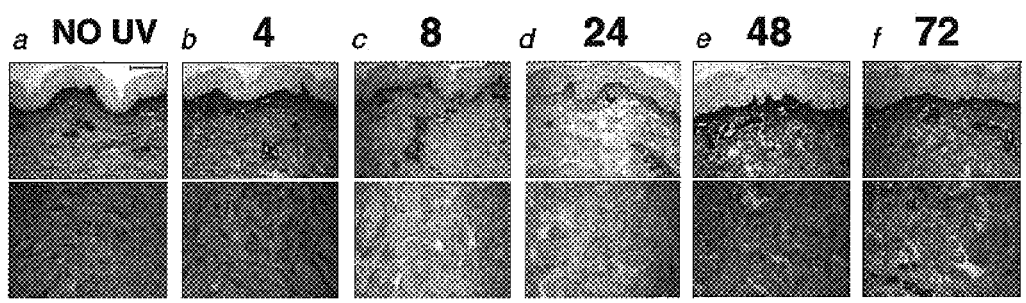
FIGS. 5A–5F depict cross-sections of biopsies of human skin stained for the presence of Type III procollagen protein as a function of time after exposure to UV radiation.

FIG. 3 is a histogram showing the results of our analysis by Western blotting for the amounts of Type I procollagen protein and the pN collagen precursor protein (i.e., the procollagen having had its carboxy terminus cleaved extracellularly) in skin at specific times after exposure to UV radiation. The abscissa in FIG. 3 is normalized to a value of 1.0 for unexposed skin. In this figure it can be seen that the amounts of these proteins are essentially the same before exposure and about 4 hours later, and drop precipitously by 8 hours after exposure. The amounts of procollagen and pN precursor protein stay at very depressed levels at least one day after UV exposure, and return to about half of their original amounts three days after exposure.

FIGS. 4A–4E depict results for the analysis for Type III procollagen mRNA analogous to FIGS. 1A–1E. Similarly, they show that the Type III procollagen mRNA is essentially absent from the skin one day after exposure to UV radiation and returns to a more normal value after about two days, and appears to exhibit a rebound effect after three days (72 hrs); that is, our analytical technique reveals that the amount of Type III procollagen mRNA is clearly greater after recovery from the UV-induced inhibition of collagen synthesis than before exposure, which can be seen by comparing FIG. 4A (pre-exposure) with FIG. 4D (2 days after exposure, essentially recovered) and with FIG. 4E (3 days after exposure, mRNA levels greater than before exposure).

FIGS. 5A–5F depict photomicrographs of biopsy cross-sections stained for Type III procollagen protein analogous to those shown in FIGS. 2A–2F. Again, these data show that eight hours after exposure to 2 MED, and through at least 24 hours after exposure, the Type III procollagen is almost absent from the skin and greatly diminished from its abundance in the skin prior to exposure. Similarly, two days after UV exposure, Type III procollagen has returned to the skin in an overabundance (an apparent rebound effect).

Figure 6:
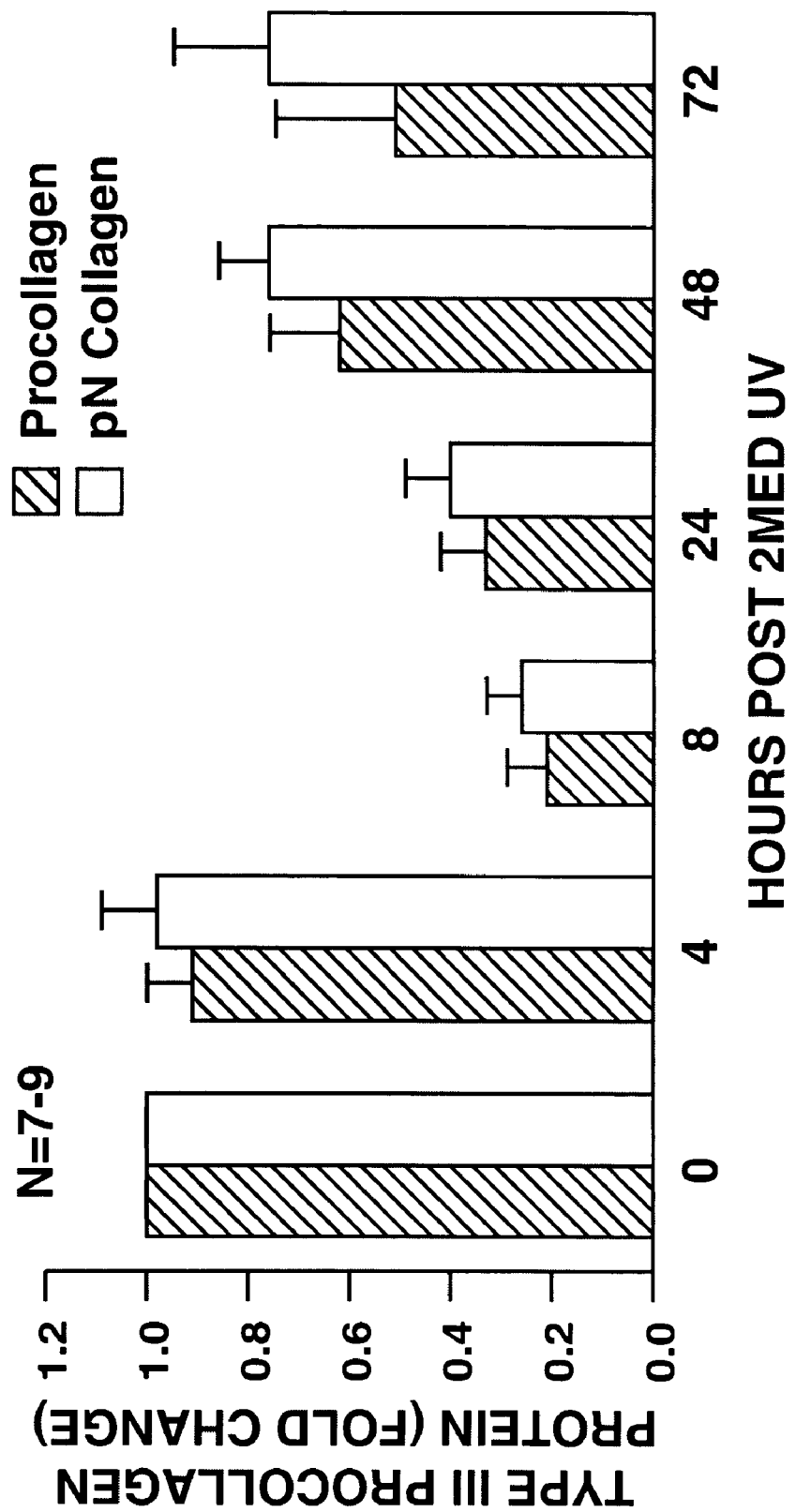
FIG. 6 is a histogram showing the results of Western analysis for Type III procollagen protein in human skin in vivo as a function of time after exposure to UV radiation.

FIG. 6, like FIG. 3, depicts our results of Western analysis blots for procollagen protein and the pN precursor protein found in biopsy samples from our volunteers taken at set times after UV exposure. Generally consistent with the other results for Types I and III procollagen, as soon as 8 hours after exposure and lasting for at least three days after exposure, the post-exposure levels of Type III procollagen protein in human skin are greatly diminished from their steady state values.

Figure 7:
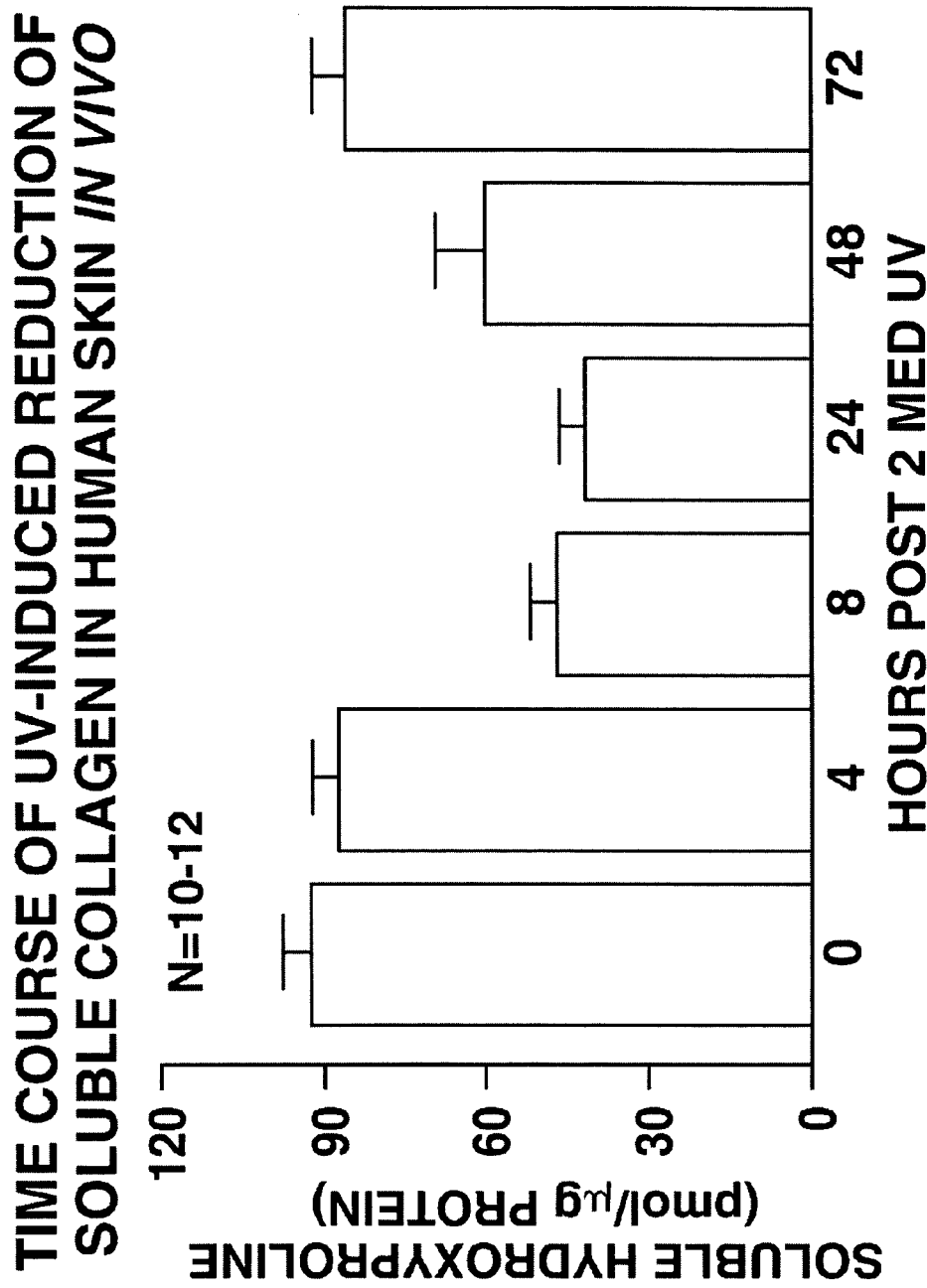
FIG. 7 is a histogram depicting the amount of soluble collagen (determined via hydroxyproline measurement) from in human skin in vivo as a function of time after exposure of the skin to UV radiation.

As mentioned above, collagen and procollagen each include the amino acid hydroxyproline, which is an uncommon amino acid, and so assays for its presence are indicative of the amount of collagen present. FIG. 7 depicts the summary of our analysis for hydroxyproline in biopsies taken from our volunteers at different times after exposure to UV radiation; the abscissa shows the soluble hydroxyproline in picomoles per microgram of total protein, indicative of the amount of soluble collagen (i.e., procollagen) in human skin. As seen in FIG. 7, the loss of soluble collagen from skin becomes detectable only after about four (4) hours, and is clearly detectable eight (8) hours after UV exposure. This deficit in the amount of soluble collagen persists at about the same level for about two days after exposure to UV radiation.

We investigated the effect, if any, on the inhibition of collagen synthesis as a function of the UV dose. Using five of our volunteers, we biopsied sun-protected skin from each and assayed the biopsy for soluble collagen by measuring the amount of soluble hydroxyproline in the sample from exposed skin compared with one from unexposed skin. We exposed different sun-protected sites on these volunteers' skin to 0.1, 0.5, 1, and 2 MEDs of UV radiation and biopsied these areas 24 hours after UV exposure to determine the effect of the UV dose on the amount of soluble collagen in the volunteers' skin. These results are shown in FIGS. 8 and 9.

Figure 8:
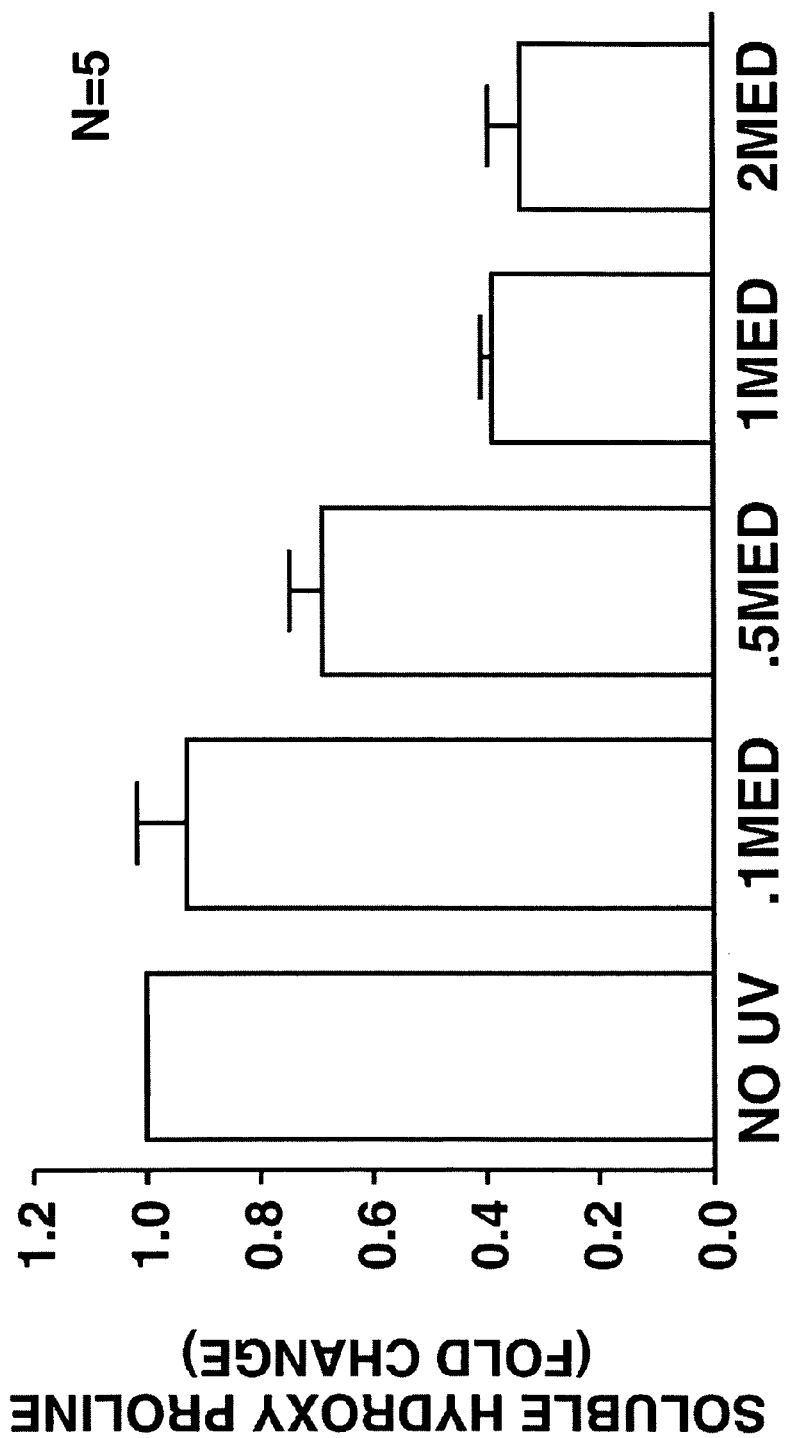
FIG. 8 is a histograph showing the amount of soluble collagen (determined via hydroxyproline measurement) from human skin in vivo as a function of the amount of UV with which the skin was irradiated.

FIG. 8 is a histograph shows our results in determining the effect of various doses of UV radiation on the loss of soluble collagen in sun-protected human skin 24 hours after exposure (measured as the amount of hydroxyproline in biopsies from our human volunteers). This figure shows that 0.5 MED of UV radiation caused a discernible loss of soluble collagen, and that an exposure to 1 MED was essentially equivalent to an exposure of 2 MED in causing a loss of soluble collagen.

Figure 9:
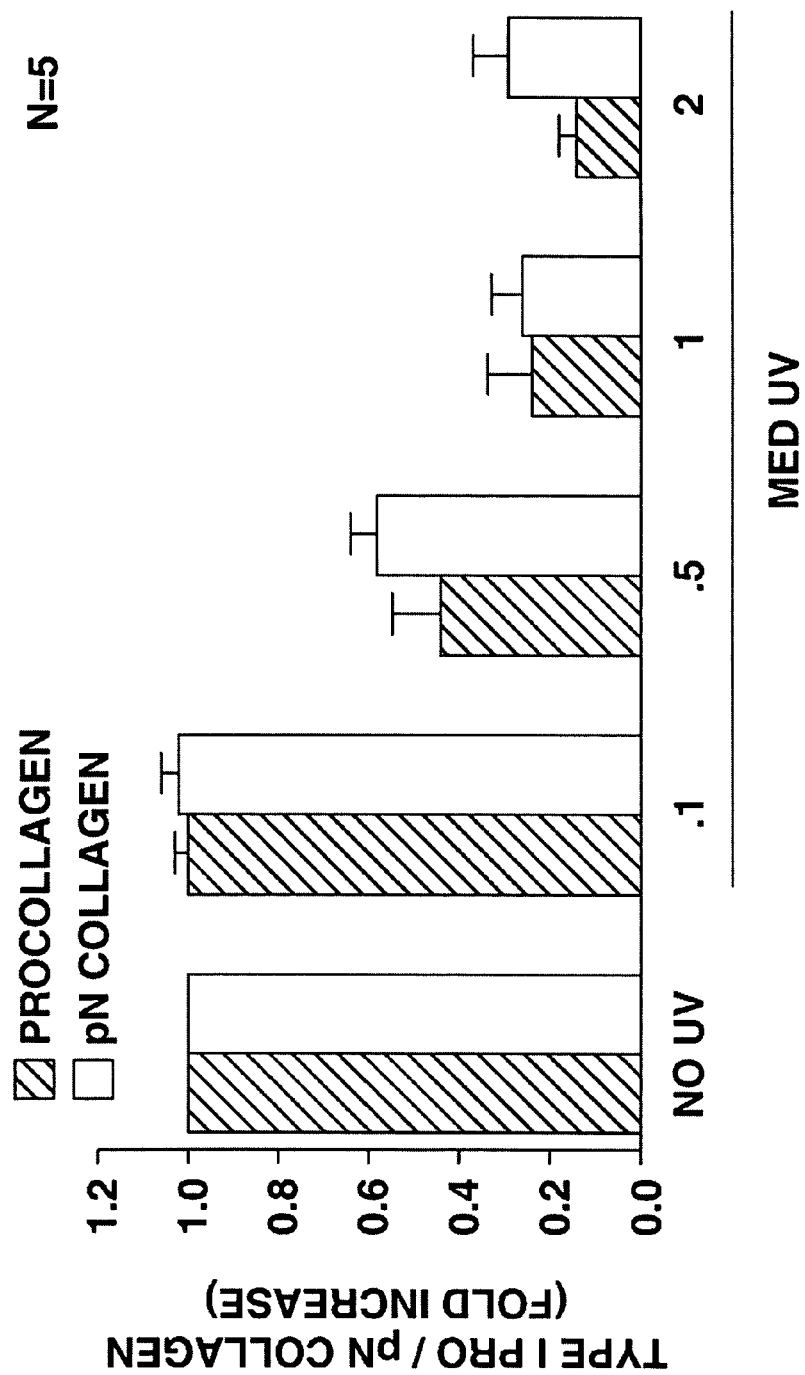
FIG. 9 depicts as a histograph the results of Western analysis for Type I procollagen protein and the pN precursor protein as a function of the amount of UV with which the skin was irradiated.

FIG. 9 is a histogram depicting a summary of our Western analysis of Type I procollagen and the pN precursor protein in human skin after exposure to the same UV doses as in FIG. 8. FIG. 9 shows that an exposure of 0.1 MED had a negligible effect on the amount of soluble collagen and Type I procollagen protein in the skin after 24 hours, while 0.5 MED had a more pronounced effect, and 1 MED was almost equivalent to 2 MED by causing a loss of about 60% of the soluble collagen and 80% of the procollagen protein and the pN precursor protein. Therefore, human skin exposed to sub-MED UV radiation will have a resulting loss of collagen synthesis even without the occurrence of erythema. These results mean that incidental exposure to UV radiation that is insufficient to cause erythema, the type of exposure that would be expected to occur on a daily basis (such as going to and from work or school), nevertheless results in a loss of collagen synthesis.

These results show that exposure of human skin to one MED of UV radiation, or less, leads to a rather complete loss of the mRNA that codes for the production of Types I and III procollagen in the cell as well as a rather complete loss of procollagen Types I and III in the dermal matrix. We have shown in the aforementioned patent applications on photoaging that MMPs are elevated after 2 MEDs of UV exposure. While not desirous of being constrained to a particular theory of operation, we believe that the loss of procollagen is due either to its conversion to collagen which is then degraded by MMPs, or to some other mechanism that is preventing the synthesis of procollagen or its conversion to insoluble collagen. It is clear that there is a concomitant loss of mRNA signalling for collagen synthesis that is caused by exposure to UV radiation. The reduced signalling could be due to reduced transcription of the mRNA, or increased degradation of the procollagen mRNA that is produced. Regardless of the actual mechanism(s) by which procollagen mRNA and protein are reduced (which mechanism(s) is not being relied upon for a theory of patentability), it is clear the reduced mRNA signalling for the production of procollagen fails to replenish the procollagen lost in the dermal matrix after exposure to UV radiation.

Retinoid Pretreatment

We tested whether retinoids, in particular all-trans retinoic acid, would have any effect on the loss of procollagen mRNA and/or the procollagen proteins in human skin after exposure to UV radiation. (Unless otherwise noted, the retinoic acid used in the experiments described herein was all-trans.) Separate areas of skin from each of our volunteers were treated with either 0.1% retinoic acid in vehicle or with vehicle alone; the vehicle was composed of a mixture of ethanol and polyethylene glycol in a 70:30 volumetric ratio. Thereafter, these areas of skin were exposed to 2 MEDs (typically) of UV radiation and then biopsied at specific times after the exposure; the biopsies were analyzed as described previously. The site of the volunteers' skin to be exposed to UV radiation was treated prior to UV exposure with either the all-trans retinoic acid or the control vehicle. Pretreatment times of eight hours before exposure did not appear to significantly prevent reduction in collagen synthesis, whereas pretreatment times of 24 hours before exposure gave the results we describe below (in which a reduction in collagen biosynthesis was prevented). Nevertheless, it should be understood that a period of pretreatment with retinoid more than eight and less than twenty-four hours before UV exposure may likely be sufficient to prevent the reduction in collagen biosynthesis we have observed. Furthermore, it should be understood that in all of the following examples treatment with a retinoid (e.g., "retinoic acid-treated") or the vehicle (e.g., "vehicle-treated") should each be understood as pretreatment 24 hours before UV exposure.

Figure 10:
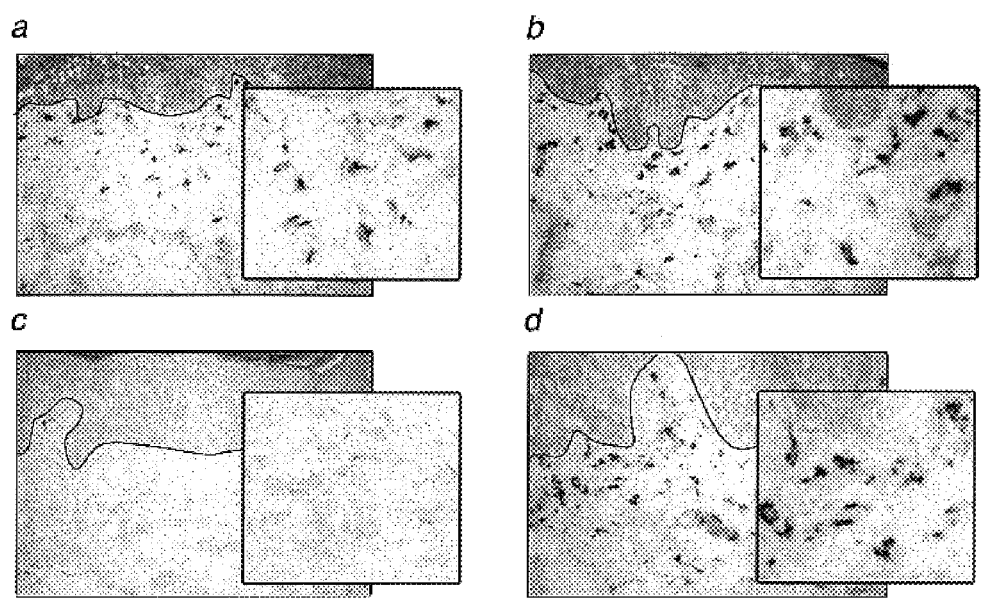
FIGS. 10A–10D depict cross-sections of biopsies of human skin treated with either retinoic acid or a vehicle alone and stained for the expression of Type I procollagen mRNA, both before and after exposure of the skin to UV radiation.

Our invention on the use of retinoids to protect against the UV-induced loss of procollagen Types I and III is more graphically depicted in FIG. 10, which shows stained biopsy cross-sections (analogous to those shown in FIG. 1) of vehicle- and retinoid-treated skin prior to UV exposure, and then after UV exposure. FIG. 10 shows cross-sections stained for Type I procollagen mRNA (the dermis-epidermis junction has been delineated electronically with a solid line). FIG. 10A is vehicle-treated skin and FIG. 10B is all-trans retinoic acid-treated skin, both prior to UV exposure. In this pair of photographs, the procollagen mRNA is expressed in the various fibroblasts in the dermis; while the retinoic acid-treated ("RA" caption in the figure) skin shows darker staining, the number and density of the fibroblasts producing the mRNA for procollagen biosynthesis are essentially the same in both. After UV exposure, the skin treated with only the vehicle evidences a gross reduction in mRNA, as shown in FIG. 10C, and so it can be inferred that no procollagen is being synthesized. However, skin pretreated (24 hours) with a retinoid and then exposed to UV radiation does not appear to evidence any loss in the mRNA signalling necessary for procollagen biosynthesis, as shown in FIG. 10D. Comparing FIGS. 10C and 10D, it is striking to note that the retinoid-treated skin appears unaffected by exposure to UV radiation, to the extent that Type I procollagen mRNA is expressed to the same degree after UV exposure as before. The skin lacking the retinoid treatment (vehicle-treated) shows essentially a complete inhibition of procollagen synthesis.

Figure 11:
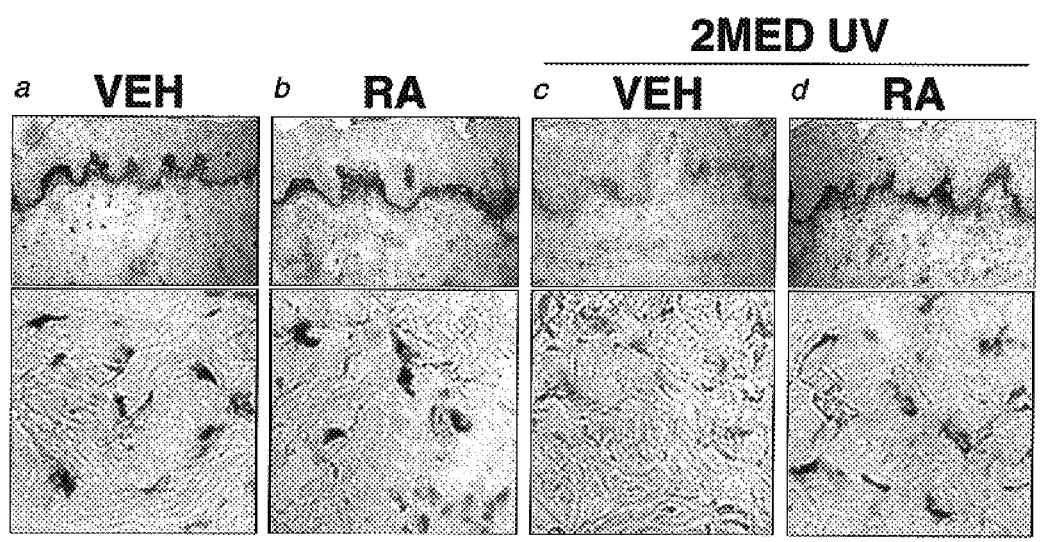
FIGS. 11A–11D depict cross-sections of biopsies of human skin stained for the expression of Type I procollagen protein in human skin after treatment with retinoic acid or a vehicle alone, both before and after exposure of the treated skin to UV radiation, and which shows the protective effect of retinoids on procollagen protein synthesis.

FIGS. 11A–11D depict the immunohistological staining of cross-sections of skin from our volunteers stained for the presence of Type I procollagen protein wherein the skin was pretreated with either a retinoid or the vehicle alone and biopsied both before and after UV exposure. In FIGS. 11A and 11B the presence of the Type I procollagen protein can be seen in patterns similar to those shown in FIG. 2A; the protein is present in the fibroblasts in the dermis and at the dermis-epidermis junction. There is no appreciable difference between the patterns for FIGS. 11A and 11B. Biopsies taken 24 hours after exposure to UV radiation of 2MED yield striking differences between the control and the retinoid treated areas. FIG. 11C shows the control (vehicle-treated) skin biopsy in which the staining at the dermis-epidermis junction is significantly less than before exposure, and there is almost no staining in the dermis (implying that there is no procollagen in the fibroblasts). On the other hand, the retinoid-treated section shown in FIG. 11D has significantly more staining for Type I procollagen protein at the dermis-epidermis boundary, and in the fibroblasts in the dermis, than the control biopsy. The staining in FIG. 11D is comparable, though slightly reduced, to that in FIGS. 11A and 11B before UV exposure. Accordingly, retinoids prevent the reduction in Type I procollagen protein and the Type I procollagen mRNA that occurs both in fibroblasts and at the dermis-epidermis junction after exposure to UV radiation.

Figure 12:
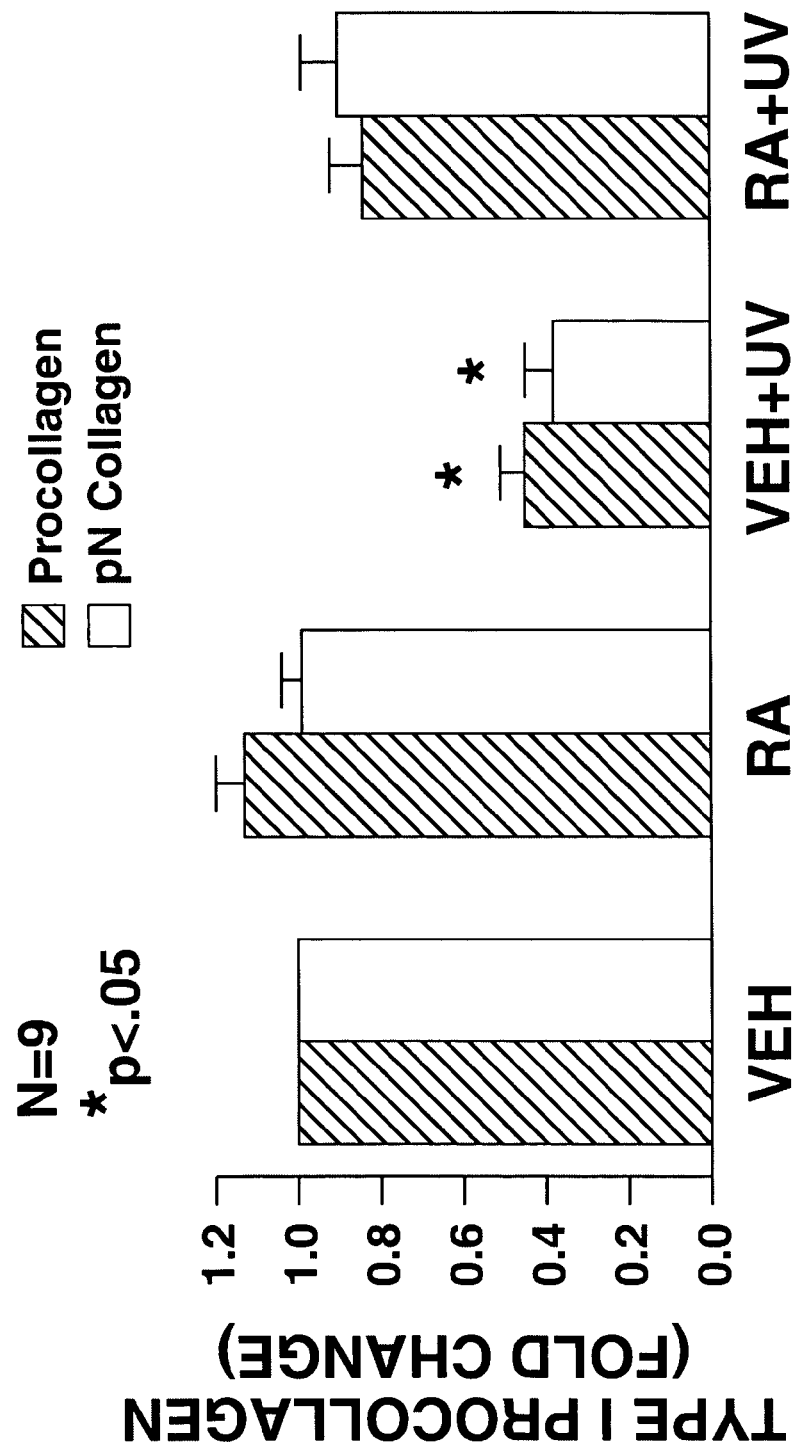
FIG. 12 is a histograph showing the results of Western analysis for the amount of Type I procollagen protein and the pN precursor protein in human skin both before and after exposure to UV radiation where the exposed skin had been treated previously with retinoic acid or a vehicle alone.

FIG. 12 is a histogram depicting our results of Western blot analyses of biopsies from our volunteers where the skin was pretreated with retinoic acid or the vehicle alone, biopsied, exposed to UV radiation, and biopsied again. As shown, prior to UV exposure the vehicle-treated area has an amount of Type I procollagen and the pN collagen precursor that have been normalized to a value of 1.0. Unexposed retinoic acid-treated skin had essentially the same amounts of Type I procollagen and the pN precursor protein. The biopsies of UV-exposed skin taken 24 hours after exposure to 2 MEDs show that the vehicle-treated areas had less than half the amounts of Type I procollagen protein and pN collagen precursor protein than were present before exposure. These results are consistent with those discussed previously. The retinoic acid-treated areas, though, showed very little loss of both the Type I procollagen and the pN collagen precursor protein; both values were greater than 80% of the control.

Figure 13:
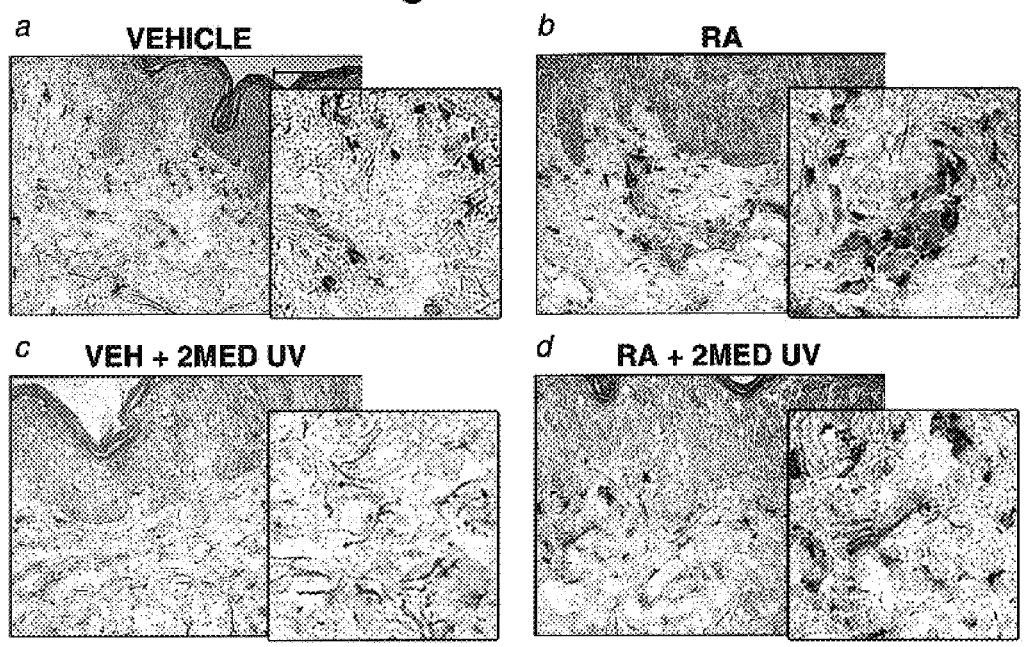
FIGS. 13A–13D depict cross-sections of biopsies of human skin treated with either retinoic acid or a vehicle alone and stained for the expression of Type III procollagen mRNA, both before and after exposure of the pretreated skin to UV radiation.

The use of retinoids to protect against the UV-induced loss of Type III procollagen is also graphically depicted in FIG. 13, which shows biopsied cross-sections (analogous to those shown in FIG. 4) of vehicle- and retinoid-treated skin prior to UV exposure and then after UV exposure, stained for the expression of Type III procollagen mRNA. Type III procollagen mRNA is expressed in fibroblasts in the dermis, prior to UV exposure, in both vehicle-treated (FIG. 13A) and retinoic acid-treated (FIG. 13B) skin. After exposure to UV radiation, the vehicle-treated skin showed essentially a complete absence of the expression of the Type III procollagen mRNA (FIG. 13C), whereas the retinoid-treated skin showed little, if any, reduction in the expression of Type III procollagen mRNA (FIG. 13D).

Figure 14:
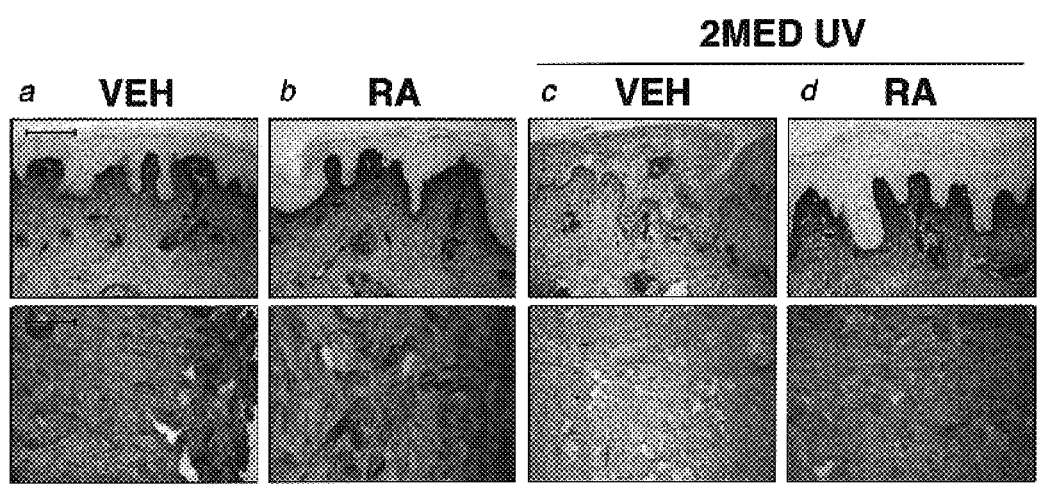
FIGS. 14A–14D depict cross-sections of biopsies of human skin treated with either retinoic acid or a vehicle alone and stained for the expression of Type III procollagen protein, both before and after exposure of the pretreated skin to UV radiation.

FIGS. 14A–14D are analogous to FIGS. 13A–13D, as just described, but are stained for the presence of Type III procollagen protein. As shown in FIGS. 14A and 14B, in stained biopsies of the control and retinoid-treated areas, prior to exposure to UV radiation, the Type III procollagen protein is present throughout the dermis. Twenty-four hours after exposure to 2 MEDs of UV radiation, the amount of Type III procollagen protein is dramatically diminished throughout the dermis in the control (vehicle-treated) biopsy section (FIG. 14C). In stark contrast, the retinoid-treated area after exposure to UV radiation (FIG. 1D) has almost the same pattern and intensity of staining as shown in FIGS. 14A and 14B prior to UV exposure. Therefore, the topical administration of a retinoid prior to UV exposure prevents the reduction in Type III procollagen protein (FIG. 14) and the Type III procollagen mRNA (FIG. 13) that occurs after exposure to UV radiation.

Figure 15:
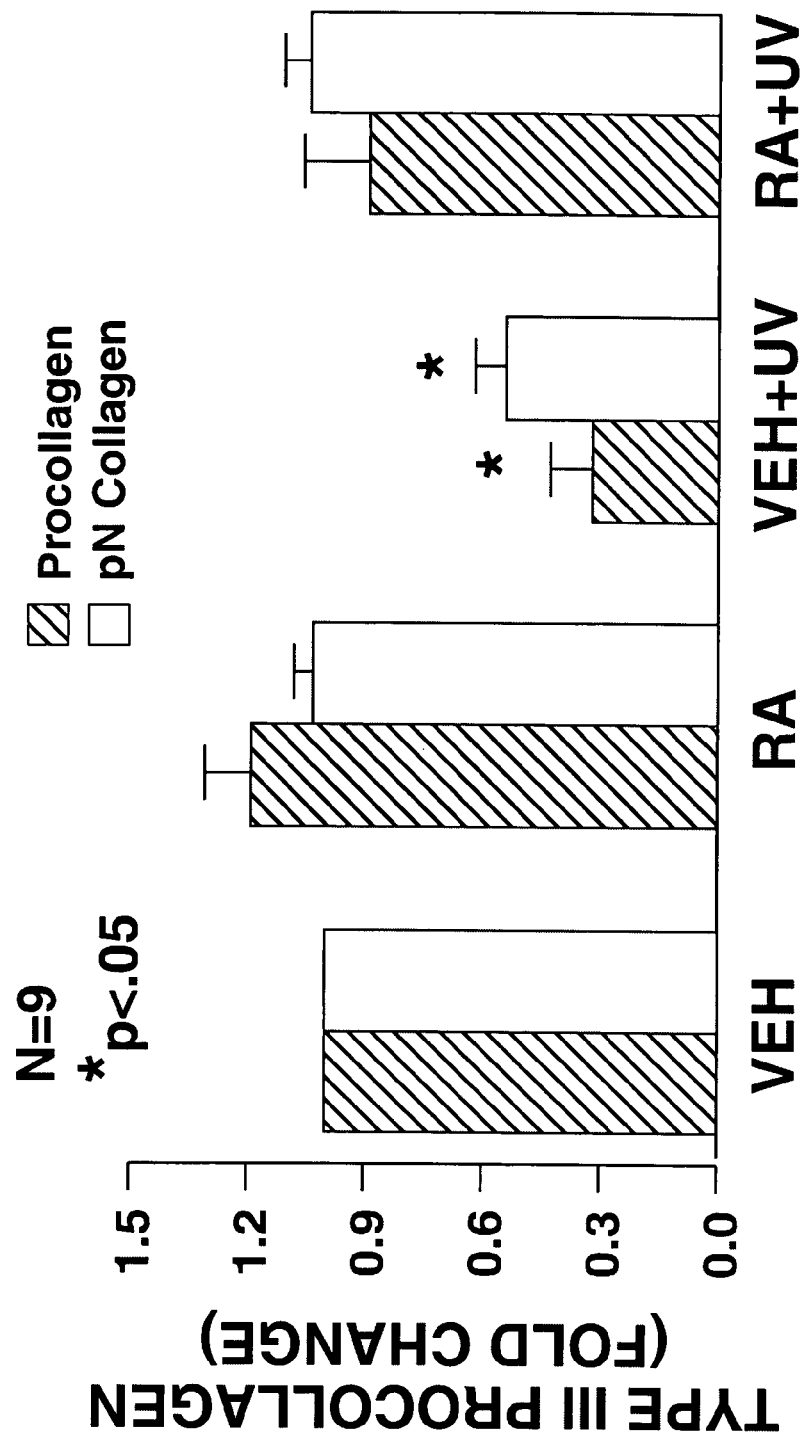
FIG. 15 is a histograph showing the results of Western analysis for Type III procollagen protein and the pN precursor protein in human skin in vivo where the skin was pretreated with either retinoic acid or a vehicle alone and then exposed to UV radiation.

FIG. 15 presents a histograph of our results for Western analysis of the Type III procollagen protein and the pN collagen precursor protein (analogous to FIG. 12) in human skin treated with either retinoic acid or vehicle alone prior to exposure, and biopsied both before and after UV exposure. Again, prior to UV exposure both vehicle (VEH) and retinoic acid (RA) treated skin had essentially the same amounts of these proteins. After 2 MEDs of UV exposure, the amounts of these proteins in the skin had been essentially halved, as shown by the VEH+UV bars. However, the retinoic acid-treated UV-irradiated sections (RA+UV) had essentially the same amounts of these proteins as both the control and the retinoic acid-treated areas prior to exposure.

Figure 16:
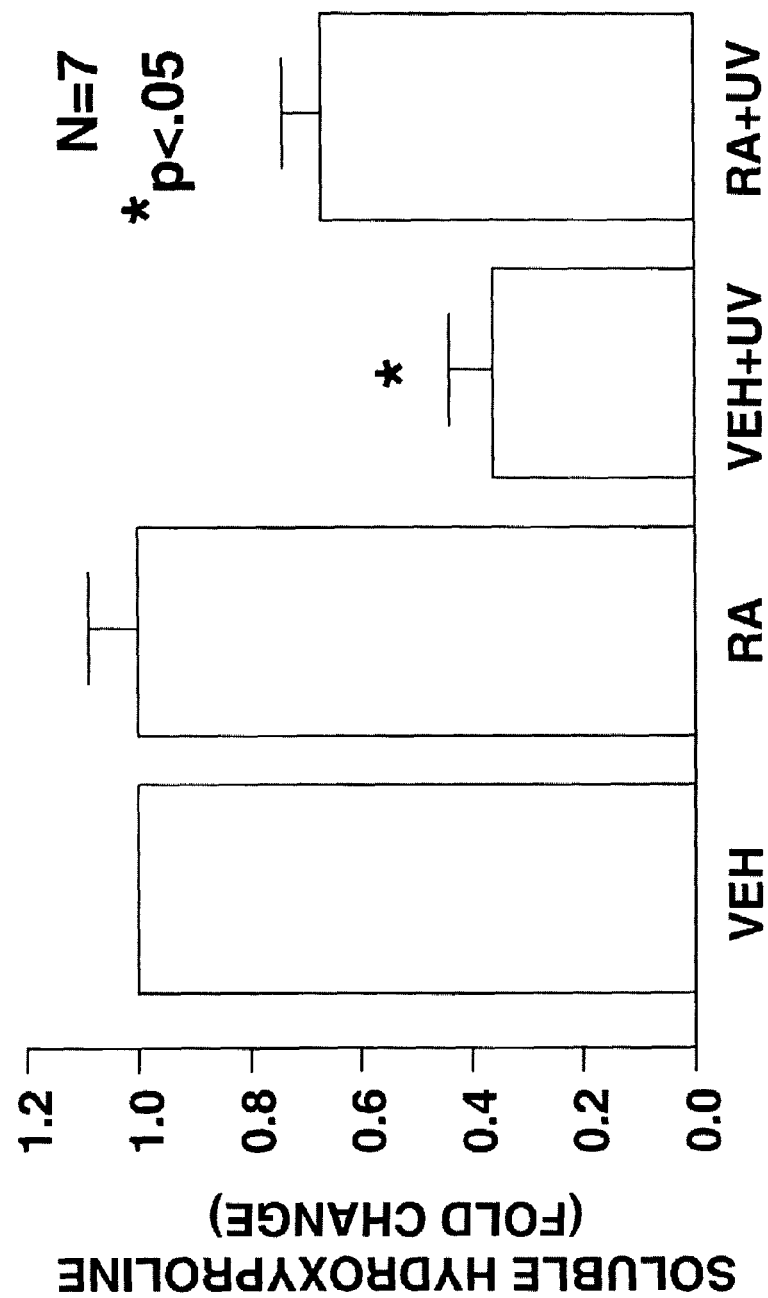
FIG. 16 is a histograph depicting our results of the assayed amount of soluble collagen (measured via hydroxyproline content) in human skin in vivo treated with either retinoic acid or a vehicle alone, both before and after exposure to UV radiation.

We also assayed the biopsies from our volunteers for soluble collagen (measured as hydroxyproline content) in vehicle- and retinoid-treated skin, both before and after UV exposure. As shown in FIG. 16, prior to exposure, the amount of soluble collagen in the control and retinoid-treated skin were each about the same (the vehicle-treated skin being normalized to a value of 1.0). After UV exposure, the vehicle-treated skin (VEH+UV) had only about 40% of the soluble collagen as was present prior to exposure. The retinoid-treated area (RA+UV) still had reduced amounts of soluble collagen when compared with skin prior to UV exposure, yet the levels were almost twice what was found in the vehicle-treated/UV-exposed skin.

Figure 17:
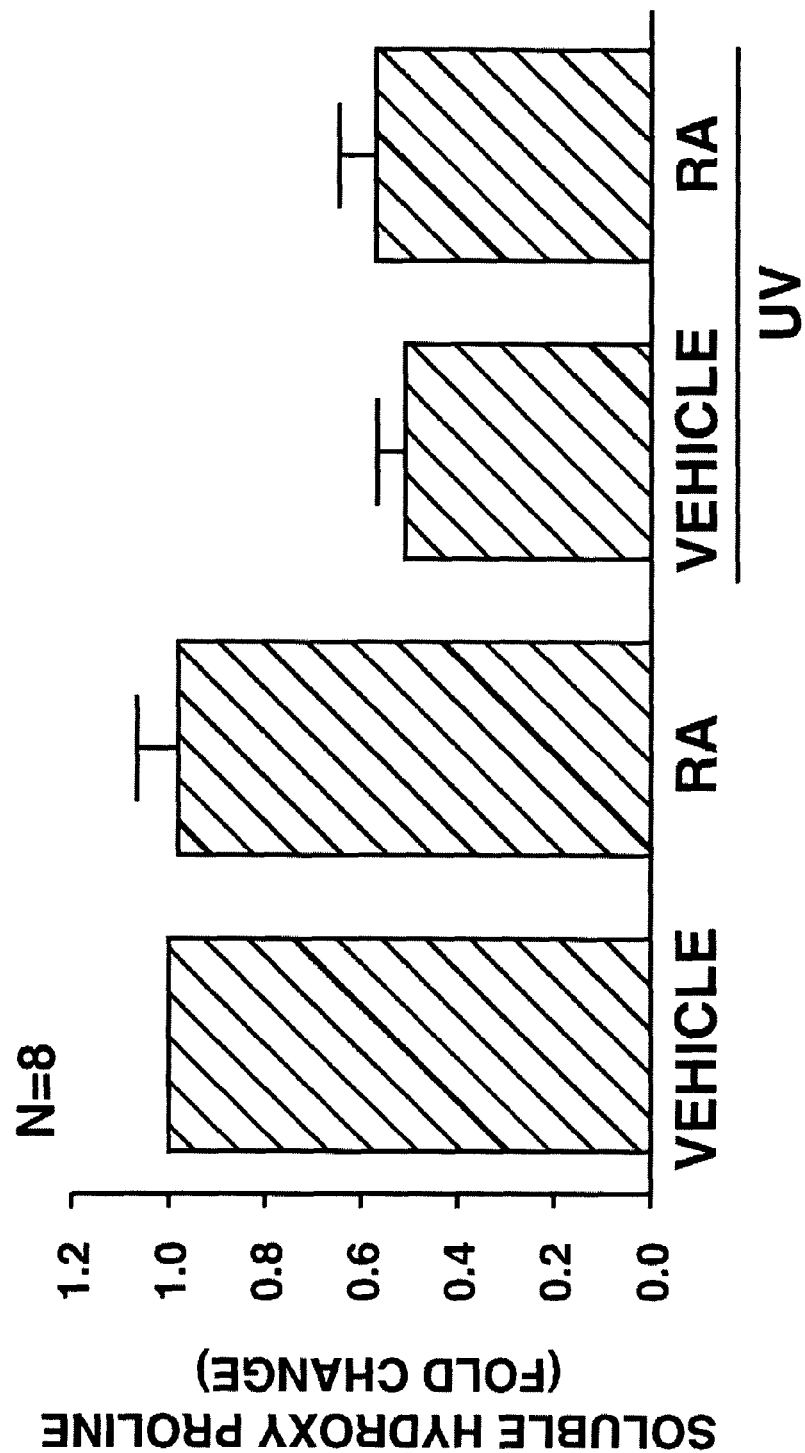
FIG. 17 is a histograph depicting our analysis for soluble collagen (determined via hydroxyproline content) in human skin both before and after exposure to UV radiation, wherein the skin was pretreated 8 hours before exposure with either vehicle alone or a retinoid.

As mentioned above, the area of the volunteers' skin to be treated with a retinoid prior to UV exposure was pretreated 24 hours prior to exposure. We pretreated certain volunteer's sun-protected skin with 0.1% all trans retinoic acid 8 hours prior to exposure to 2 MEDs of UV radiation. As shown in FIG. 17, the level of soluble collagen in sun-protected skin (as measured by hydroxyproline content) in vehicle- and retinoid-treated skin after 8 hours and without exposure to UV radiation was the same (normalized to a value of 1.0). Pretreatment 8 hours prior to exposure to 2 MEDs provided no discernible benefit: as the right hand part of FIG. 17 shows, the amount of soluble collagen 24 hours after UV exposure where the exposed skin had been pretreated with a retinoid 8 hours before exposure was essentially the same in the retinoid-treated and the control (vehicle-treated) skin. Thus, as mentioned above, to prevent UV-induced loss of collagen synthesis using a retinoid, pretreatment 24 hours before exposure yields the desired prophylactic effect, whereas pretreatment 8 hours before exposure yields no significant prophylaxis.

Figure 18:
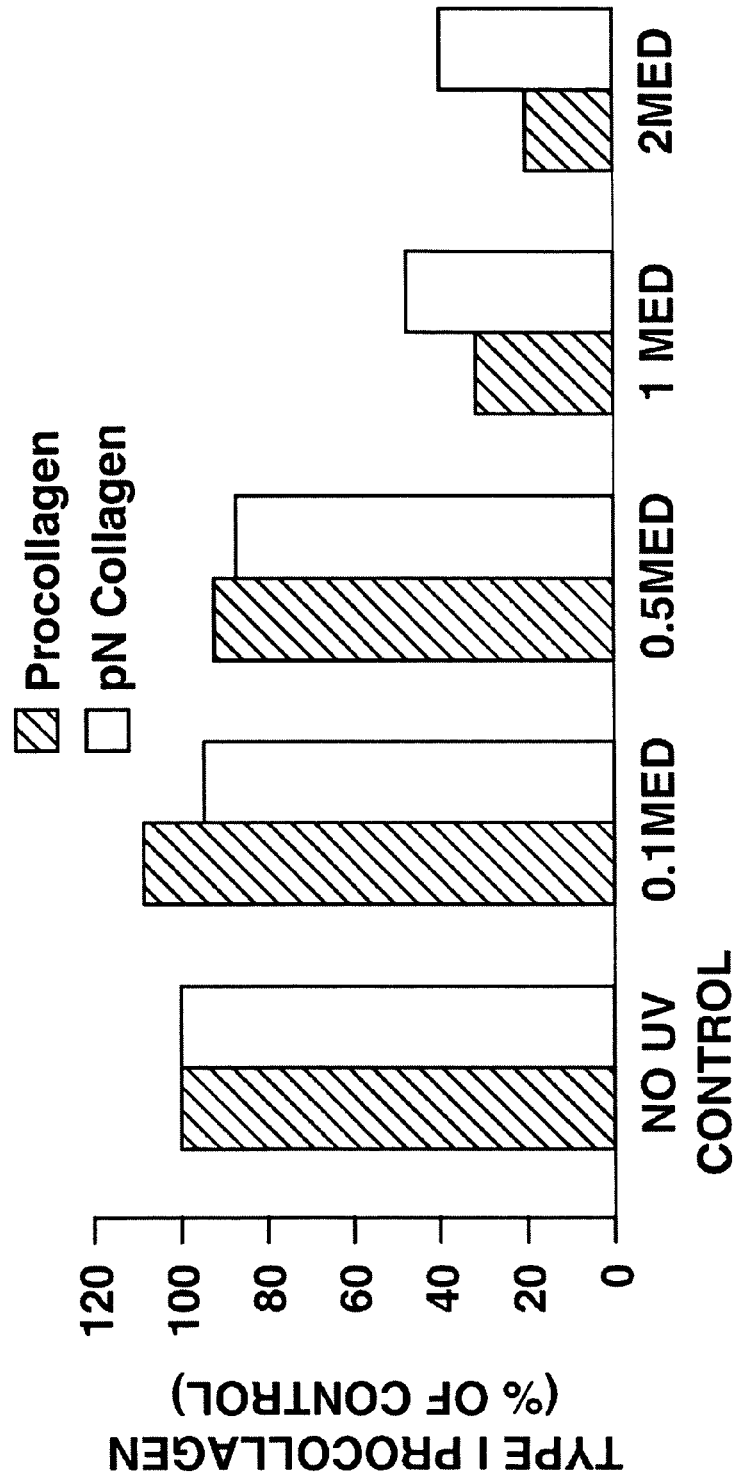
FIG. 18 is a histograph depicting our analysis for Type I procollagen protein and the pN precursor protein in human skin after exposure to different doses of UV light using a light source that approximates the output from the sun.

The foregoing examples were performed using the bulbs and filters noted above. We have determined that such a system provides UV radiation with about twenty times less UVA radiation than normal sunlight for the same incident energy basis. The radiation from those tubes comprises about 50% UVB, about 25% UVA, and about 25% IR/visible. In natural sunlight, only about 4–5% of the UV radiation is UVB; the remainder is UVA. We have now used a "solar simulator" that provides, at 290–400 nm (UVA and UVB range), solar radiation having relative amounts of UVA and UVB that are equivalent to that found in natural solar (i.e., a ratio of UVA:UVB of about 9:1). We have examined the effect of this solar-simulated UV irradiation (mimicking the spectral output of the sun) on type I procollagen protein levels in human skin in vivo. As shown in FIG. 18, we found that exposure doses of 1MED and 2MED solar-simulated UV causes significant reductions of type I procollagen protein, as was shown previously with UV exposure from a predominantly UVB source. Accordingly, this confirms that UV radiation from the sun causes loss of procollagen in human skin in vivo.

Figure 19:
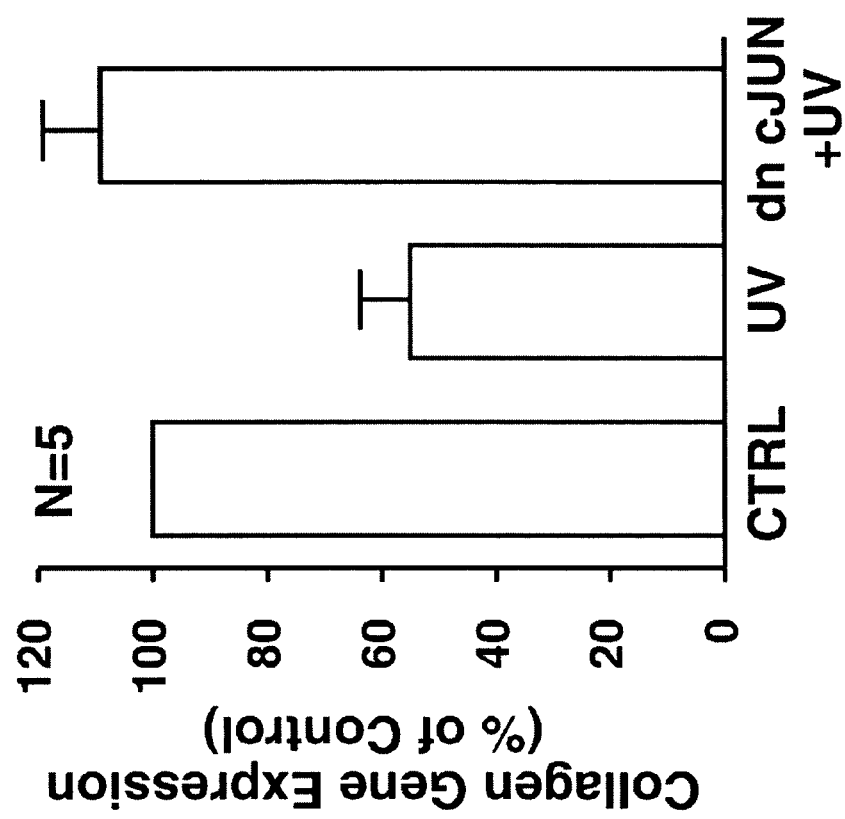
FIG. 19 is a histograph depicting our analysis of collagen gene expression determined via a reporter gene after that gene has been introduced into human skin fibroblasts and those cells then irradiated.

As described above, in human skin the cells that produce type I procollagen are fibroblasts. We have utilized cultured human skin fibroblasts to better understand how UV causes inhibition of procollagen synthesis in human skin. UV irradiation inhibits type I procollagen gene expresion in cultured human skin fibroblasts, like it does in human skin in vivo. UV irradiation also induces transcription factor c-JUN in cultured human skin fibroblasts, like it does in vivo; induction of c-JUN results in the generation of MMPs that degrade collagen. We introduced into human skin fibroblasts a collagen (type I alpha 2) reporter gene for type I procollagen; namely, the gene-772 COL1A2 deletion plasmid (described by H. Ihn, E. D. LeRoy, and M. Trojanowska in *J. Biological Chem.*, 272:24666–672,1997) was inserted using a dominant negative c-jun plasmid named TAM-67 (described by P. H. Brown, T. K. Chen, and M. J. Birrer in *Oncogene*, 9(3):791–9,1994). As transformed, the dominant negative plasmid results in the production of a non-functional c-JUN factor that interferes with the normal c-JUN functioning, while it is non-functional it effectively neutralizes the functional c-JUN in the cell. Thus, the reporter gene is expressed when collagen synthesis genes are expressed. FIG. 19 shows the results obtained by exposing these transformed cells to UV radiation. The control (CTRL) is shown to provide a baseline of active collagen gene expression that occurs normally in these modified cells. After the cells have been irradiated with UV light from the solar simulator (at about 30 mJ/cm$^2$), the reporter gene expression is analyzed and, as shown in the figure, it is reduced to about 50%; thus, solar radiation reduces collagen gene expression. Turning to the transformed cells in which the mutant c-JUN interferes with expression of normal c-JUN, after exposure to UV radiation (from the aforedescribed bulbs, not the solar simulator) there is no reduction in collagen gene expression. Thus, in these altered cells, when transcription of the collagen gene occurs, the reporter gene that interferes with c-JUN is activated, thereby preventing the inhibition of collagen synthesis. These data indcate that c-JUN mediates inhibition of type I procollagen gene expresion by UV radiation. Accordingly, agents, like retinoids, that block induction of c-JUN by UV radiation would be effective in protecting skin exposed to UV from loss of procollagen. Other inhibitors of c-JUN are described below.

In summary of the foregoing, we have shown that UV radiation depletes the amount of collagen, procollagen protein, the pN precursor protein, and the procollagen mRNA in the skin and inhibits the synthesis of collagen. We have shown that sub-MED levels of UV radiation, as well as supra-MED levels of exposure, also result in a loss of soluble collagen, procollagen, the pN precursor, and mRNA signalling. We have shown that the decrease in procollagen protein levels is not discernible until some time after exposure. And we have shown that retinoids protect human skin in vivo against the UV-induced inhibition of collagen synthesis. It should be appreciated that the present invention is useful for preventing the UV-induced inhibition of collagen synthesis in both skin that has no discernable photoaging and in skin which has existing photodamage (either in the long term through chronic exposure or in the short term, such as after a sunburn had at the beach). Whether or not the skin has actual or visible photodamage, exposure to the sun will result in an inhibition of procollagen synthesis. For skin that does not appear to be photodamaged, use of this invention will prevent inhibition of procollagen synthesis. Sun-damaged skin, in which procollagen synthesis has been inhibited, is in the process of healing, and further exposure to the sun will effectively prevent healing by both degrading collagen that has been replaced as part of the healing process, and by continuing to cause inhibition of collagen synthesis. Accordingly, this invention is useful on all skin, regardless of the degree of existing photodamage.

Retinoids useful in practicing the present invention include those such as disclosed in U.S. Pat. No. 4,877,805 and the dissociating retinoids that are described by Fanjul et al. in Nature (1994) 372:104–110. Retinoids typically include natural and synthetic analogs of vitamin A (retinol), vitamin A aldehyde (retinal), vitamin A acid (retinoic acid (RA)), including all-trans, 9-cis, and 13-cis retinoic acid), etretinate, and others as described in EP-A2-0379367, U.S. Pat. No. 4,887,805, and U.S. Pat. No. 4,888,342 (the disclosures of which are all incorporated herein by reference). Various synthetic retinoids and compounds having retinoid activity are expected to be useful in this invention, to the extent that they exhibit retinoid activity in vivo, and such are described in various patents assigned on their face to Allergan Inc., such as in the following U.S. Pat. Nos.: 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos.: 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like. The disclosures of all of the foregoing and following patents and literature references are hereby incorporated herein by reference. While retinol is the preferred compound for topical administration, effective derivatives of retinol that would be expected to be useful for practicing this invention specifically include retinal, retinoic acid (including all-trans, 9-cis, and 13-cis isomers) and derivatives thereof (such as 7,8-didehydroretinoic acid), and others as described by Kligman et al., the disclosure of which is incorporated herein by reference, including cosmetically acceptable salts, esters, reverse esters, and ethers thereof, conjugates thereof, and mixtures thereof.

The effective amount of the active ingredient applied to the skin is preferably in the range of about 0.001–5 wt. %, more preferably about 0.01–2 wt. %, still more preferably 0.1–1 wt. %. Compositions are formulated to provide preferably about 5 µg±2.5 µg/cm² skin when applied. For example, a preferred composition for use in this invention is Retin-A® retinoic acid gel and cream (available from Ortho Pharmaceuticals) available presently for the treatment of acne vulgaris, in strengths of from 0.01% to 0.1%; the vehicle preferably includes, depending upon the particular formulation, at least one of butylated hydroxytoluene, alcohol (denatured with t-butyl alcohol and brucine sulfate), stearic acid, isopropyl myristate, polyoxyl 40 stearate, stearyl alcohol, and the like, and compatible mixtures thereof.

Other compounds useful for practicing this invention include those that inhibit the signalling in the kinase cascade pathways, such as the stress-induced pathways (SAPs) at or upstream of the presence of c-JUN, that result in the formation of c-JUN. It is preferred that these compounds be administered topically. Exemplary compounds that are inhibitors of c-JUN include geranyl geranyltransferase inhibitors and lisofylline, which inhibit activation of the JNK cascade. Compounds such as SB202190 (described by Lee, J. C., et al., Nature (1994) 372:739–746) and PD98059 (described by Dudley, D. T., et al., Proc. Nat. Acad. Sci. (USA) (1995) 92:7686–7689) that inhibit specific kinases in the SAP cascade are also useful in this invention. Other compounds that are likely to inhibit the formation of c-JUN are cell surface receptor inhibitors that prevent or diminish the increase in c-JUN occurring after exposure to UV radiation. Such receptor inhibitors (commercially available from BIOMOL Res. Labs., Inc., Plymouth Meeting, Pa.) include: antagonists of ionophore and G protein-coupled receptors (such as suramin, also known as an antiprotozoal); and antagonists of epidermal growth factor receptors (such as: AG-494; Erbstatin analog; Genistein; Lavendustin A; Tyrphostins 1, 9, 23, 25, 46, 47, and 51; and PD 153035).

Antioxidants can be viewed as inhibitors of collagen synthesis inhibition by UV radiation. While not desirous of being constrained to a particular theory, it is believed that such compounds work by quenching or otherwise reducing free radicals and reactive oxygen species which initiate or lead to the kinase cascades that result in c-JUN formation, which leads to MMP production and, it is believed, inhibition of collagen synthesis. Antioxidants useful in this invention include glutathione and its precursors, such as N-acetyl cysteine (NAC), more broadly $N-CH_3(CH_2)_nCO$ cysteine (wherein n is an integer from zero to eight, more preferably not more than 4), and related compounds and derivatives thereof as described in U.S. Pat. No. 5,296,500 (the disclosure of which is incorporated herein by reference). Antioxidants also include: (i) lipid-soluble compounds such as β-carotene and its derivatives, other carotenoids, and vitamin E and related tocopherols; (ii) water-soluble compounds such as vitamin C and derivatives thereof (e.g., ascorbyl glucoseamine), glutathione, and NAC; and (iii) other compounds such as one of the pigments that makes tomatoes red, lipoic acid, genistein, and ebselen and other selenium compounds. Glutathione and its precursors, such as N-acetyl cysteine (NAC), more broadly $N-CH_3(CH_2)_nCO$ cysteine (wherein n is an integer from zero to eight, more preferably not more than 4), and related compounds and derivatives thereof are described in U.S. Pat. No. 5,296,500 (the disclosure of which is incorporated herein by reference).

The compositions useful in this invention can include one or more compounds that function as a sunblock (e.g., zinc cream) or sunscreen (e.g., oxybenzones, alkoxycinnamates, and the like), as described above; a preferred sunscreen is PARSOL® 1789, alone or in combination with PARSOL MCX or another sunscreen. PARSOL® 1789 (also known as PARSOL A) is 4-t-butyl-4'-methoxydibenzoylmethane, which is described in U.S. Pat. No. 4,387,089 (the disclosure of which is incorporated herein by reference). (PARSOL MCX and PARSOL MOX are both trademarks for 2-ethylhexyl p-methoxycinnamate, a UVB blocker commonly used in commercial sunscreens, and disclosed in U.S. Pat. No. 4,713,473, the disclosure of which is incorporated herein by reference).

The foregoing description is meant to be illustrative and not limiting. Various changes, modifications, and additions may become apparent to the skilled artisan upon a perusal of this specification, and such are meant to be within the scope and spirit of the invention as defined by the claims.

Methods Used in the Examples

Histology and morphometry. Replicate 4-mm punch biopsies were obtained from buttock or hip skin of each individual. Formalin-fixed tissue pieces were sectioned, stained with hematoxylin and eosin, randomized and blinded. The sections were examined using an Olympus BX40 microscope in conjunction with a Sony DCX-151 high-resolution camera. Blocked areas 200 μm on a side were isolated using NIH Imager software and epidermal height was assessed at four sites (25 μm apart) in each of two such areas. The same two blocked areas were used for epithelial cell counts. The number of interstitial cell nuclei (i.e., nuclei below the dermis-epidermis junction, not associated with capillaries) over the entire histological section was determined as a measure of dermal cellularity. The same blinded sections were scored for connective tissue fiber spacing, thickness, degree of disorganization and depth of disorganization, using a scale of 1–9 for each parameter.

Northern analysis of RNA. Total RNA (e.g., for procollagen α1 (III)) was isolated from skin samples by guanidinium hydrochloride lysis and ultracentrifugation (as described by G. J. Fisher et al., "Cellular, immunologic and biochemical characterization of topical retinoic acid-treated human skin," *J. Investig. Dermatol.*, 96:699–707 (1991)). Northern analysis of total RNA (40 μg/lane) with randomly primed $^{32}$P labelled cDNA probes for the particular mRNA to be determined were performed as described by G. J. Fisher et al. (in "All trans retinoic acid induces cellular retinol-binding protein in human skin in vivo," *J. Investig. Dermatol.*, 105:80–86 (1995)). Type III procollagen mRNA was determined using reverse transcriptase polymerase chain reaction.

Western analysis of proteins. Type I procollagen and pN collagen precursor protein, as well as Type III procollagen were detected in skin extracts by Western analysis as described by G. J. Fisher et al. (in "Immunological identification and functional quantitation of retinoic acid and retinoid X receptor proteins in human skin," *J. Biol. Chem.*, 269:20629–20635 (1994)).

Immunoreactive proteins were visualized by enhanced chemiluminescence detection and quantified by laser densitometry, or by enhanced chemifluorescence detection and quantified by a Storm imager (Molecular Dynamics, Sunnyvale, Calif.).

Immunohistology: Immunihistology of Type I and Type III pN collagens was performed as has been described by Griffiths, C. E. M., et al., *N. Engl. J. Med.*, 329:530–535 (1993). Type I pN collagen was detected with mouse monoclonal IgG1 antibody (SP1.D8; available from Univ. of Iowa Dept. of Biological Sciences Developmental Studies Hybridoma Bank, Iowa City, Iowa) raised against the aminopropeptide region of human Type I procollagen (Foellmer, H. G., et al., *Euro. J. Biochm.*, 134:183–189 (1983)). Type III pN collagen was detected with affinity-purified rabbit polyclonal antibody to aminopropeptide of Type III procollagen (identical to that used for Western analysis). Appropriately diluted IgG1 was used as control for SP1.D8 antibody and rabbit serum for Type III procollagen antibodies.

In Situ Hybridization: Digoxigenin-containing sense and antisense riboprobes to detect human type I and Type III procollagen RNA (mRNA) were synthesized with the use of T3 and T7 ribonucleic acid polymerases. Frozen skin sections (5 μm) were mounted, fixed, treated, and hybridized as described by Fisher, G. H., et al., *J. Invest. Dermatol.*, 105:80–86 (1995). Hybridization signals were detected immunohistochemically with the use of alkaline phosphatase-conjugated antidigoxigenin antibody.

Hydroxyproline Analysis: hydroxyproline analysis using the Amino Acid Analyzer Model 420H (Applied Biosystems, Foster City, Calif.) automates pre-column phenylthiocarbamyl-amino acid (PTC-M) analysis. The Model 420H analyzer first hydrolyzes proteins to liberate free amino acids. Once hydrolyzed, the free amino acids are derivatized with phenylisothiocynanate (PITC) to form PTC-AA derivatives. A reverse-phase column in a temperature-controlled oven separates the PTC-AAs. Concentration of hydroxyproline in the skin extract was determined based upon a hydroxyproline standard.

What is claimed is:

1. An article of manufacture for effecting a diminution in the reduction in collagen biosynthesis in human skin mediated by exposure of the skin to UV radiation, comprising: a packaged first composition comprising an effective amount of a retinoid in a pharmaceutically acceptable carrier suitable for topical administration; and indicia associated with said packaged composition indicating that said composition is applied to the skin at least about eight hours prior to exposure to UV radiation to effect said diminution.

2. The article of claim 1, wherein the retinoid in the first composition is all-trans retinoic acid, retinol, or a mixture thereof.

3. The article of claim 1, wherein the retinoid in the first composition prevents a diminution in Type I procollagen synthesis.

4. The article of claim 1, wherein the retinoid in the first composition prevents a diminution in Type III procollagen synthesis.

5. The article of claim 1, wherein indicia advises that the source of the UV radiation is the sun.

6. The article of claim 1, further comprising a second composition selected from the group consisting of a sunscreen, a sunblock, an antioxidant, or a combination thereof.

7. The article of claim 1, further comprising as a second composition an antioxidant.

8. The article of claim 1, further comprising as a second composition a combination of (i) an antioxidant and (ii) a sunscreen or sunblock.

9. The article of claim 6 or 8, wherein the sunscreen comprises 4-t-butyl-4'-methoxydibenzoylmethane.

10. The article of claim 9, wherein the sunscreen is a combination of 4-t-butyl-4'-methoxydibenzoylmethane and 2-ethylhexyl p-methoxycinnamate.

11. The article of claim 6, 7, 8, 9, or 10, wherein said first composition and said second composition are provided in separate formulations.

12. The article of claim 6, 7, 8, 9, or 10, wherein said first composition and said second composition are provided in a single formulation.

13. A topical pharmaceutical composition for preventing the reduction in collagen biosynthesis in human skin mediated by exposure of the skin to UV radiation, comprising an effective amount of an inhibitor of c-JUN and a pharmaceutically acceptable carrier therefor, wherein said composition is topically administering to the skin prior to the exposure of the skin to UV radiation by an amount of time effective to prevent a UV-induced reduction in collagen biosynthesis.

14. The composition of claim 13, wherein the inhibitor is a geranyltransferase inhibitor, lisofylline, SB202190, PD98059, an antagonist of an ionophore, G protein-coupled receptor, or epidermal growth factor receptor.

15. The composition of claim 14, wherein the antagonist is suramin, AG-494, Erbstatin analog, Genistein, Lavendustin A, Tyrphostins 1, 9, 23, 25, 46, 47, or 51, or PD 153035.

16. The composition of claim 15, wherein the antagonist is genistein.

* * * * *